United States Patent [19]

Lucas et al.

[11] 4,092,068
[45] May 30, 1978

[54] SURFACE SENSOR

[75] Inventors: John Martin Lucas; Serge Gracovetsky, both of Montreal, Canada

[73] Assignee: Domtar Inc., Montreal, Canada

[21] Appl. No.: 683,477

[22] Filed: May 5, 1976

[51] Int. Cl.² .................. G01N 21/00; G01N 21/18; G01N 21/30
[52] U.S. Cl. ........................ 356/73; 162/198; 250/563; 250/572; 356/167; 356/199; 356/210
[58] Field of Search ........... 356/73, 199, 200, 210, 356/212, 167; 162/198; 250/559, 563, 571, 572

[56] References Cited

U.S. PATENT DOCUMENTS

| | | | |
|---|---|---|---|
| 2,947,212 | 8/1960 | Woods | 250/572 |
| 3,591,291 | 7/1971 | Greer et al. | 356/199 |
| 3,834,822 | 9/1974 | Stapleton et al. | 356/200 |
| 3,984,189 | 10/1976 | Seki et al. | 356/200 |

FOREIGN PATENT DOCUMENTS 894,570   4/1962   United Kingdom ................ 356/200

*Primary Examiner*—Vincent P. McGraw
*Attorney, Agent, or Firm*—C. A. Rowley

[57] ABSTRACT

A surface sensor utilizing a light source for projecting light onto a travelling surface and thereby illuminate a limited area of said surface is combined with at least two angularly spaced sensors and arranged to detect light reflected. Signals are generated in accordance with the amount of light received and these signals are processed to obtain at least one of (a) an indication of topographical surface characteristics of the web surface while suppressing the effects of changes in reflectivity of the surface and (b) indication of the change in reflectivity while suppressing the effects of topography of the surface.

6 Claims, 24 Drawing Figures

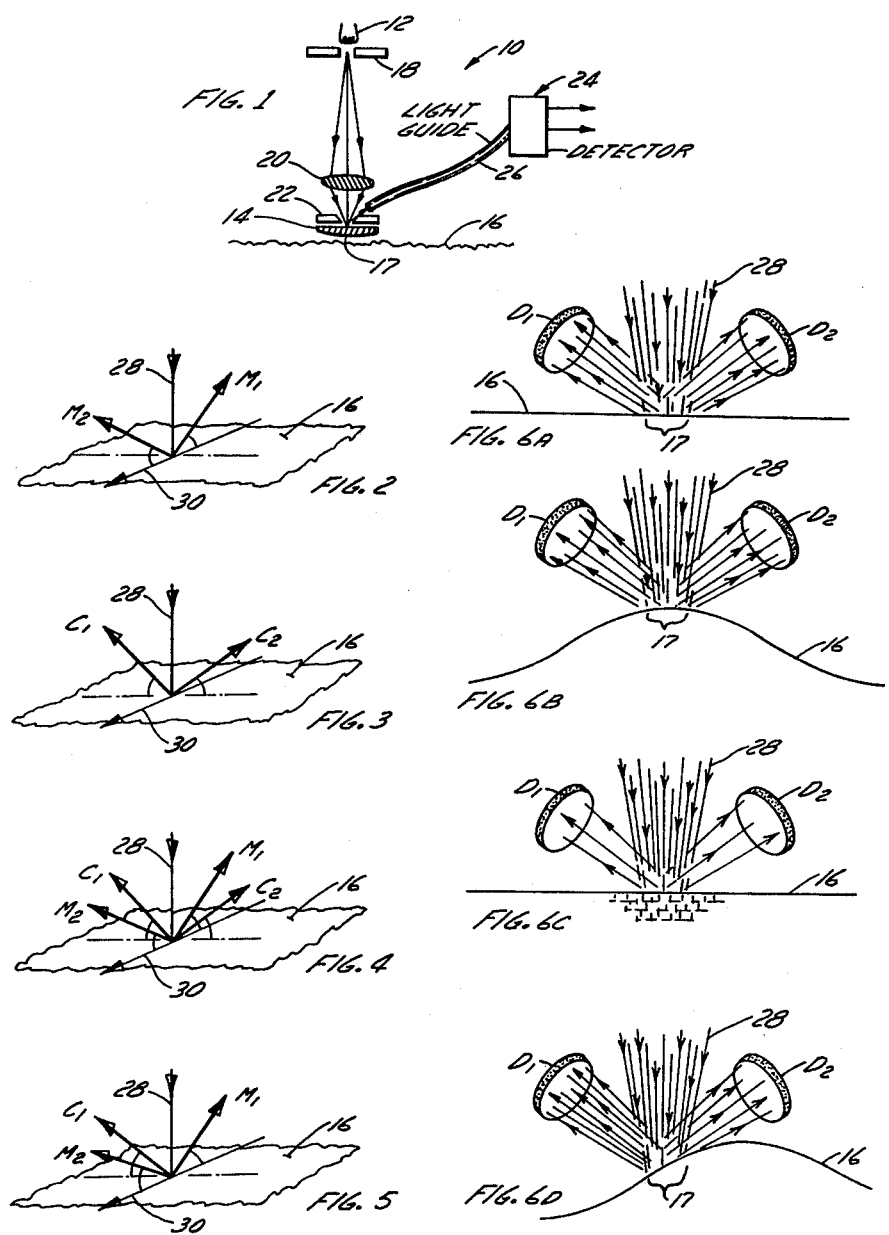

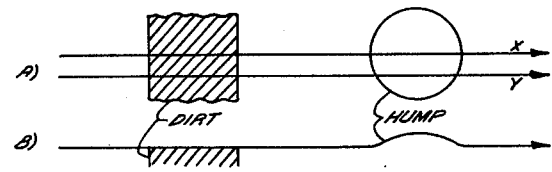
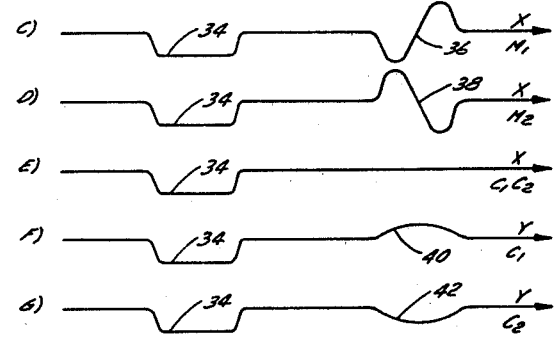
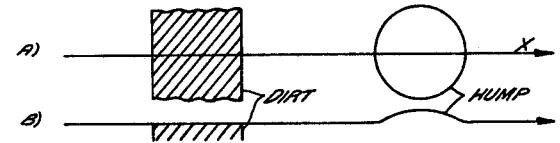
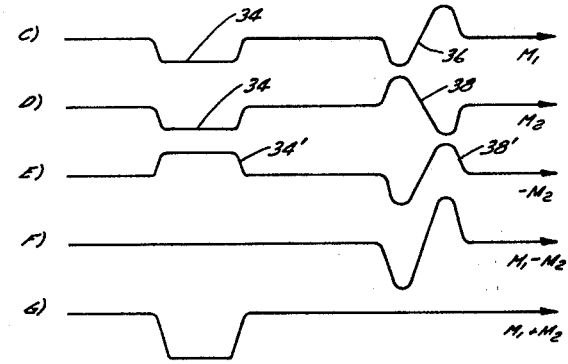
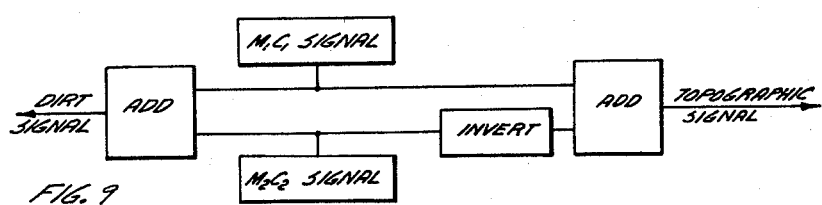

SURFACE SENSOR

FIELD OF THE INVENTION

The present invention relates to a sensor for determining surface characteristics of a travelling surface. More particularly the present invention relates to a surface sensor for determining small scale surface characteristics of a travelling paper web relating to geometry and reflectivity e.g. roughness and dirt.

By roughness (or its opposite smoothness) it is generally understood the geometric property of the surface which may be defined as a deviation from (or in the opposite case closeness to) an ideally flat plane. In the case of paper or board the deviations that are perceived as a roughness are on a small scale and occur as topographic features of the surface (peaks or valleys) having dimensions in the order of about 0.01 to 5 mm. in the plane of the paper and about 0.01 to 1 mm in a direction normal to the plane. Deviations of larger dimensions in the plane of the paper are generally attributed to properties other than roughness and may come, e.g. under the designation of waviness, or of variations in thickness, etc.

BACKGROUND OF THE PRESENT INVENTION

Sensors for determining the degree of roughness by optical means do not provide generally the amount of information available from the device of the present invention. Also discrimination between a dirt particle and a topographical feature is sometimes difficult.

Devices have been described in the patent literature, for example, Canadian Pat. No. 617,188 issued March 28, 1967 discloses a device for detecting surface conditions on a travelling web. This device is sensitive to longitudinal striations on the surface of the web and operates by directing a light beam obliquely onto the surface in a direction generally perpendicular to the length of the striations on the web and sensing the amount of light reflected.

Canadian Pat. No. 836,242 issued Mar. 10, 1970 to Joyce discloses a device for determining surface characteristics of a paper sheet in particular for determining a wire mark on a paper sheet. One of the concepts of this invention is to project a light through a web and to use a mask, having a plurality of apertures corresponding at least partially to the pattern of the wire mark, in combination with detecting means which generates signals and to process the signals to obtain an indication, for example, of web speed. The device does not convey general information of the topographical configuration of the web.

U.S. Pat. No. 3,591,291 discloses a device for detecting the roughness of a relatively smooth surface by directing a collimated beam of light against the surface and mounting one light sensitive element at the angle of reflection of said beam from the surface, and further light sensitive elements in the same plane as the illuminating and reflected beams but at different angles to the surface. The signal generated by the light sensitive element located at the angle of reflection is compared with signal developed by one of the other light sensitive elements to give an indication of surface roughness. This device is based on the assumption that the amount of light diffused and diffracted from the peaks on the smooth surface is a function of the inclination of the slopes of those peaks and that those inclinations are functions of the height of the peaks and therefore that the amount of diffusion and diffraction of the light by the peaks on a relatively smooth surface is a measure of the height of the peaks. The device is operated by positioning it on the surface and comparing the light signals with no relative movement between the surface being measured and the sensor.

In an earlier device invented by the inventors of the instant application, the roughness of a moving surface was sensed by projecting a beam of light at a low angle of an inclination to sequentially illuminate small areas on the surface, collecting scattered light reflected from the small areas, generating electrical signals in accordance with the amount of light collected and analyzing these signals to provide, for example an index of roughness. This device is not in general suited for discriminating topography from dirt particles.

SUMMARY OF PRESENT INVENTION

It is an object of the present invention to provide a surface analyser capable of extracting information relating to the topography of a surface and/or detecting "dirt" spots or blemishes on the surface (spots of significantly different reflectivity than the average surface).

Broadly the present invention comprises a light source for directing light to illuminate a limited area of a moving surface to be inspected, at least a pair of detector means for detecting light reflected at different angles from said area, means for generating signals in accordance with the amount of light sensed by each of said detectors, means for continuously processing said signals for obtaining at least one of (a) indications of the topography of said surface while substantially reducing the effect of the local differences in reflectivity from the surface and (b) spots of lower or higher reflectively on said surface while substantially reducing the effects of the topography.

Objects of the present invention may be obtained using the various different combinations of equipment for measuring variations in light scattering with time from a small illuminated area (an area equivalent to a circle 0.1 to 0.2 mm in diameter but in certain applications as large as about 1 mm in diameter) using at least two angularly spaced detectors.

The area illuminated may equal the total area detected with the remainder of the instrument in darkness so that the detectors sense substantially only the light reflected from the illuminated area. Alternatively a larger area may be illuminated and the light focused onto the detectors such that they detect only a portion of the area illuminated (the portion of the area being preferably an area equivalent to a circle 0.1 mm to 0.2 mm in diameter), the said detectors will be focused on the same portion of the illuminated area.

It is preferred to use the first technique outlined above, i.e. to illuminate only the area to be detected as this simplifies the equipment and it is this equipment that will be described in more detail in the preferred arrangement.

The light source is preferrably positioned to project light substantially perpendicular to the surface being examined. The detectors preferably will be arranged to detect light at points spaced around the illuminated area at 90° or multiples of 90°.

Preferably the detectors are in pairs positioned one on either side of the illuminated area, i.e. 180° apart, and for example aligned with the direction of said relative movement between the surface and the sensor to provide machine direction surface information. When 3 or more detectors are used it is preferred to provide at least one detector arranged 90° to the first pair of detectors whereby at least one detector may be used to determine the cross machine surface information.

Preferably but not essentially the detectors are positioned at the same angle of between 20° and 60° to the surface of the web to be sensed.

BRIEF DESCRIPTION OF THE DRAWINGS

Other features, objects and advantages will be evident from the following detailed description of the preferred embodiments of the present invention taken in conjunction with the accompanying drawings in which:

FIG. 1 is a schematic illustration of a sensor head of the present invention;

FIGS. 2 to 5 inclusive illustrate schematically different arrangements of detectors in the sensor head.

FIGS. 6a, b, c and d schematically illustrate the effects of different surface configurations on the light detected.

FIGS. 7a, b, c, d, e, f and g schematically illustrate the scan that would be obtained by the various sensors passing along the scan lines X or Y of FIG. 7a and b.

FIGS. 8a, b, c, d, e, f and g schematically illustrate the processing of the signals to provide topographical and dirt indications, and FIG. 9 is a schematic illustration of a system for processing signals derived from a pair of detectors positioned on opposite sides of the light source (illuminated area), i.e. 180° apart.

DESCRIPTION OF THE PREFERRED EMBODIMENT

Referring to FIG. 1 the basic elements of the sensor 10 of the present invention comprise a light source 12 for directing a light beam through a window 14 thereby to illuminate at any instant an area 17 (see FIGS. 1 and 6) of the surface 16 to be scanned. In the illustrated arrangement the source 12 projects light through an aperture 18 which limits the area of the source 12, and a lens 20 focusses the light through an aperture 22 and the window 14 to illuminate the area 17 on the surface 16. The beam of light from source 12 is projected onto the surface 16 in a direction perpendicular or substantially perpendicular to the surface 16. The area 17 which is illuminated at any given instant is no greater than an area equivalent to a circle of about 1 mm in diameter and preferably 0.1 to 0.2 millimeters in diameter.

Detectors such as that schematically illustrated at 24 are suitably positioned about the sensor 10 to detect light reflected from the spot or area 17 illuminated on the surface 16 by the light source 12. A single detector 24 has been shown in FIG. 1, however, at least two such detectors will be provided. These detectors are preferably inclined at an angle of about 20° - 60° to the surface 16 with each detector preferably being the same angle to the surface.

It is often more convenient to convey the light to the detectors 24 by a suitable optical means comprising, for example, a fibre light guide 26. The aperture 22 limits the stray light entering the light guides 26 and thus detectors 24.

FIGS. 2, 3, 4 and 5 illustrate various combinations of illuminator beam and detectors. The illuminator beam is schematically illustrated by the arrow 28 while the various reflected beams that are sensed by the detectors 24 are indicated by the designation M1, M2 and C1, C2.

These designations M & C are intended to indicate machine direction and cross machine direction, respectively. The direction of web travel, i.e. the machine direction of the surface is indicated by the arrow 30.

FIG. 2, illustrates sensing the two reflected beams M1 and M2 by suitable detectors 24 (not illustrated), FIG. 3, sensing the two beams C1 and C2, and FIG. 4, the four beams, M1, M2, C1, C2 so that topographical characteristics are viewed from two directions, for example, the cross machine and machine directions. FIG. 5 illustrates an arrangement wherein three beams, M1, M2 and C1 are sensed which also views the topography from two directions. Obviously the cross machine reflected beams, C1 and C2 and a single machine direction beam could be used to obtain a similar result.

The operation of the various detectors will now be explained with reference to FIGS. 6a, b, c, and d. It will be seen that when the illuminator beam 28 projects light perpendicular to the average slope of the illuminated area 17 of the surface 16 and when the detectors D1 and D2 are arranged at the same angle to the surface 16, scattered light reflected to detectors D1 and D2 will be substantially equal (FIG. 6a) even if the area 17 is at the top or crest of a hill (FIG. 6b) or bottom of the valley. It will also be apparent from FIG. 6c that if the beam 28 is reflected from a dirt spot the amount of light detected by detectors D1 and D2 will be equal but the intensity of the reflected light and therefore the magnitude of the signal will be considerably reduced. On the other hand if the average inclination of the area 17 is not perpendicular to the beam 28 then the amount of light reflected to and sensed by the detectors D1 and D2 will not be equal and the imbalance will be indicative of the slope of the surface relative to the light beam.

FIG. 7 illustrates a pair of scan lines X and Y crossing a dirty area and a hump as shown in plan and elevation in FIGS. 7a and 7b respectively. Assuming that the M1 and M2 are from detectors arranged in the machine direction, i.e. direcion travel of the scans and C1 and C2 are in the cross machine it is apparent from FIG. 7c, d, e and f that the output of detectors M1, M2, C1 C2 are all reduced in the areas 34 where the dirt is scanned, i.e. the total reflected light to the detectors M1 and M2, C1 and C2 is reduced by the presence of the dirt particle. As the sensor moves along scan X (over the center line of a hump) the detector M1 detects a decreasing amount of light and then an increasing amount of light with the intensity increasing to a point higher than the amount of light that is sensed when the inclination of the area 17 is perpendicular to the beam 28 and then decreasing back to the average, as indicated by the numeral 36. The output M2 as the sensor traverses the hump as indicated at 38 is a mirror image of the output 36.

It will be noted that the output of C1 and C2 as the sensor head moves relative to the surface along Scan line X traversing the center line of the hump do not provide and indication that a hump is present since the reflected light received by the detectors will be the same along the hump. However, on Scan line Y (part way up the hump) as indicated in FIG. 7f the output C1 on one side of the Scan line shows an increase in the amount of light detected along a curve substantially matching with the shape of the hump (Section 40) whereas the output C2 on the opposite side shows a decrease in the amount of light reflected (Section C12 FIG. 7f). These sections as indicated in FIGS. 7f and g at 40 and 42 are substantially mirror images.

FIGS. 8a and b are similar to FIGS. 7a and b in that they illustrate the scan direction over the dirt and the hump. With the relative movement of the sensor to the surface along Scan X for example, the output M1 and M2 have been repeated in FIGS. 8c and d and the output M2 has been inverted in FIG. 8e. The inverted profile is indicated by the numerals 34' corresponds to the original trace 34 and the inverted trace 38' corresponds with the trace 38. It will be noted in FIG. 8f that when the traces 8c and e are added the signal generated by the dirt completely disappears i.e. 34' cancels 34 whereas the topographical signal is emphasized (see FIG. 8f). On the other hand if the signals or traces illustrated in FIG. 8c and 8b are added, without the trace from the signal M2 being inverted, the topographical signals disappear and the dirt signal is emphasized (see FIG. 8g).

FIG. 9 illustrates schematically by simple block diagram how signals M1 and M2 or C1 and C2 may be processed by electronic means. Signals M1 and M2, as indicated to the left in this drawing, may be added to provide a dirt signal and one of the signals, for example, signal M2 may be inverted signal added to the signal generated by M1 to give a topographical signal.

When applied for example to a paper machine the sensor may be mounted on a platform which travels across the paper web. Specifically the sensor is moved with the platform slowly across the sheet while the paper moves relatively quickly therebeneath. For example, the paper may travel at, say a 1000 ft. per minute and the sensor at a speed of half a foot per second transversely to the direction of web travel. Hence the relative movement between the paper and the scanner is at a very small angle with respect to the machine direction of the sheet.

It will be apparent that the most effective way of handling the signals generated by the sensors is over preset periods of time sufficiently long that the data collected permits meaningful statistical reduction. For example, at a relative web speed of 1000 per minute sufficient data to give an index of roughness is obtained in about one second. (Similar conditions apply to the evaluation of dirt). Hence an index of roughness is obtained about every second and since the platform is simultaneously travelling across the sheet an index of roughness is obtained every half a foot across the sheet (assuming a half a foot per second speed for traverse of the platform across the sheet). This information can be plotted or displayed to give a profile of the variation of roughness across the width of the paper machine.

It will be clear that by the use of conventional equipment to add or invert and add the signals one can obtain a clearer indication of the dirt and of the topographical configuration of the surface being sensed. The signals may be further manipulated or processed such as by appropriate frequency analysis so that other features of the surface being scanned may be detected. For example, it may well be possible to detect graininess of a paper sheet due to the pecular effect graininess has on the surface of a sheet, also printability or shrinkage may be detectable by the proper analysis of the topographical features of the web.

The sensed beams M1, M2, C1, C2 have been indicated as aligned in either the machine or cross machine direction to simplify obtaining the cross machine and machine direction profiles, however, as above indicated the detectors may be arranged at other angles. Also, the angle between pairs of detectors around the illuminated area may be varied and significant information on the topography and/or brightness be detected and evaluated by proper analysis. However, the sensitivity is reduced as the detectors approach each other and the device tends to be very difficult to use when the angle subtended at the illuminated area by the two detectors projected onto the plane of the paper is reduced to about 10°.

Modifications will be evident to those skilled in the art without departing from the spirit of the invention as defined in the appended claims.

We claim:

1. A device for obtaining a continuous indication of the topographic profile of a traveling surface of paper comprising, a light source, means for directing light from said source perpendicularly onto said traveling surface to sequencially illuminate areas of said surface no greater than 1 mm in diameter, at least a pair of detectors symetrically positioned relative to said illuminated areas to receive non-specular light reflected at substantially the same angle to said surface from an instantaneously illuminated area, said angle being in the range of 20° to 60° to said surface, the angle subtended at said illuminated area between said pair of detectors when projected onto said surface being greater than 10°, means for generating a signal from each of said detectors in accordance with the amount of light sensed by said detector, electronic means substantially continuously processing said signals by subtracting one of said signals from the other of said signals from said pair of detectors, to indicate the slope of said surface in said instantaneously illuminated area, thereby to obtain a continuous indication of the topographical profile of said surface while substantially reducing the effects of local differences of reflectivity of the surface.

2. A device as defined in claim 1 wherein said means for processing comprises means adding said signals, and means for inverting one of said signals and adding said inverted signal to another of said signals to obtain an indication of the reflectivity of said surface and said surface topography respectively.

3. A device as defined in claim 1 wherein said pair of detectors are on opposite sides of said illuminated area on a straight line substantially perpendicular to the direction of travel of said surface.

4. A device as defined in claim 1 wherein said pair of detectors are substantially aligned with the direction of movement of said surface.

5. A device as defined in claim 4 further comprising a further detector angularly spaced midway between said pair of detectors.

6. A device as defined in claim 3 wherein said means for processing comprises means adding said signals and means for inverting one of said signals and adding said inverted signal to another of said signals to obtain an indication of the reflectivity of said surface and said surface profile respectively.

* * * * *